United States Patent
Lee

(10) Patent No.: US 10,702,433 B2
(45) Date of Patent: Jul. 7, 2020

(54) EXCRETA DISPOSAL APPARATUS COMPRISING GENDER-SPECIFIC MODULE

(71) Applicant: CURACO, INC., Seongnam-si, Gyeonggi-do (KR)

(72) Inventor: Hoonsang Lee, Seoul (KR)

(73) Assignee: Curaco, Inc., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/548,150

(22) PCT Filed: Feb. 3, 2015

(86) PCT No.: PCT/KR2015/001115
§ 371 (c)(1),
(2) Date: Aug. 2, 2017

(87) PCT Pub. No.: WO2016/125926
PCT Pub. Date: Aug. 11, 2016

(65) Prior Publication Data
US 2018/0042801 A1 Feb. 15, 2018

(51) Int. Cl.
*A61G 9/02* (2006.01)
*A61F 5/451* (2006.01)
(Continued)

(52) U.S. Cl.
CPC ............... *A61G 9/02* (2013.01); *A61F 5/442* (2013.01); *A61F 5/4404* (2013.01);
(Continued)

(58) Field of Classification Search
CPC . A61G 9/00; A61G 9/02; A61G 9/003; A61G 9/006; A61G 7/0005; A61F 5/449; A61F 5/4408; A61F 5/451
(Continued)

(56) References Cited

U.S. PATENT DOCUMENTS

| 4,050,103 A * | 9/1977 | Nakao | A61G 9/006 4/144.3 |
| 6,723,078 B1 * | 4/2004 | Pennington | A61F 5/451 604/327 |
| 2007/0032765 A1 * | 2/2007 | Honda | A61F 5/451 604/347 |

FOREIGN PATENT DOCUMENTS

| JP | 2003153931 A | 5/2003 |
| KR | 20080000414 A | 1/2008 |

(Continued)

OTHER PUBLICATIONS

Machine Translation for JP2003153931.*
Int'l Search Report dated Sep. 21, 2015 in Int'l Application No. PCT/KR2015/001115.

*Primary Examiner* — Erin Deery
(74) *Attorney, Agent, or Firm* — Panitch Schwarze Belisario & Nadel LLP

(57) ABSTRACT

An excreta disposal apparatus with a gender-specific module includes a body having a seating unit corresponding in shape to the curved shape of the genital area and buttocks of a human body, a urine disposal unit corresponding to the genital area of the human body, an excrement disposal unit corresponding to the buttocks of the human body and a disposal space open toward the genital area and buttocks of the human body to take excreta discharged from the human body. A main body unit, connected to the seating unit, is mounted between the legs of the human body and has an accommodation space therein. A discharge channel is provided in the accommodation space and communicates with the disposal space to discharge the excreta in the disposal space to the outside. The body includes the gender-specific module, which is detachably provided and includes the urine disposal unit.

7 Claims, 11 Drawing Sheets

(51) Int. Cl.
  *A61G 9/00*   (2006.01)
  *A61F 5/442*  (2006.01)
  *A61F 5/44*   (2006.01)
  *A61F 5/455*  (2006.01)
  *A61F 5/453*  (2006.01)

(52) U.S. Cl.
  CPC ............ *A61F 5/4408* (2013.01); *A61F 5/451* (2013.01); *A61F 5/453* (2013.01); *A61F 5/455* (2013.01); *A61G 9/003* (2013.01); *A61G 9/006* (2013.01)

(58) Field of Classification Search
  USPC ............ 4/450, 454, 455, 456, 447; 604/327, 604/346–348, 351, 353
  See application file for complete search history.

(56) References Cited

FOREIGN PATENT DOCUMENTS

| | | |
|---|---|---|
| KR | 20120091682 A | 8/2012 |
| KR | 20120097946 A | 9/2012 |
| KR | 20130028282 A | 3/2013 |

* cited by examiner

EXCRETA DISPOSAL APPARATUS COMPRISING GENDER-SPECIFIC MODULE

CROSS-REFERENCE TO RELATED APPLICATION

This application is a Section 371 of International Application No. PCT/KR2015/001115, filed Feb. 3, 2015, which was published in the Korean language on Aug. 11, 2016, under International Publication No. WO 2016/125926 A1, the disclosure of which is incorporated herein by reference.

TECHNICAL FIELD

The present invention relates to an excreta disposal apparatus for automatically disposing an excreta discharged from a human body, and more particularly, to an excreta disposal apparatus comprising a gender-specific module that can be used by mounting different gender-specific modules depending on gender.

BACKGROUND ART

In general, since the patients or the elderly, who have mobility difficulties or who are unable to move their lower body by their own will, do not have the ability to handle their own excreta, there is an inconvenience that a guardian or a caregiver should always reside at hand.

Therefore, in order to solve such an inconvenience, an excreta disposal apparatus for collecting excreta by directly contacting the body has been researched and developed. Such an excreta disposal apparatus is designed to receive and suck a user's excreta and discharge the excreta to the outside so that the excreta can be automatically treated even if the guardian or the caregiver does not reside around the user.

However, since the disposal apparatus is designed without considering the body of the user and is concentrated only on the function of the excreta disposal, the conventional excreta disposal apparatus developed to date has a problem that the usability is very low. Generally, since a part around the buttocks or the genital area where excreta is excreted is sharply curved and the excreta disposal apparatus is difficult to adhered, there are many cases where the excreta leaks out between the human body and the excreta disposal apparatus.

In addition, the users, such as the patients or the elderly, who use the excreta disposal apparatus often live in a bed and frequently cannot change their posture on their own. When such a state persists for a long time, a bedsore occurs, so that it is necessary to periodically change the posture. However, since the posture cannot be changed in the state where the excreta disposal apparatus is worn, there is an inconvenience to remove the excreta disposal apparatus.

In addition, since the shape of the body is formed very differently according to gender, it is necessary to change the structure according to each gender. However, conventionally, there is an inconvenience in that the excreta disposal apparatus specialized for each gender has not been researched and developed.

Therefore, a method for solving such problems is required.

DISCLOSURE

Technical Problem

The present invention has been made in view of the above problems, and provides an excreta disposal apparatus capable of preventing leakage of excreta while a user wears the excreta disposal apparatus, and improving the feelings of wearing.

The present invention further provides an excreta disposal apparatus which can be free from the limitation of the behavior even when the user wears the excreta disposal apparatus.

The present invention further provides an excreta disposal apparatus which can provide a specialized structure according to each gender.

The problems of the present invention are not limited to the above-mentioned problems, and other problems not mentioned can be clearly understood by those skilled in the art from the following description.

Technical Solution

In an aspect, there is provided an excreta disposal apparatus comprising a gender-specific module, the apparatus including: a body comprising a seating unit, which has a shape corresponding to a curved shape of genital area and buttocks of a human body, comprises a urine disposal unit corresponding to the genital area of the human body and an excrement disposal unit corresponding to the buttocks of the human body, and has a disposal space open toward the genital area and buttocks of the human body so as to take excreta discharged from the human body, and a main body unit, which is connected to the seating unit so as to be mounted between legs of the human body and has an accommodation space therein; and a discharge channel, which is provided in the accommodation space and communicates with the disposal space so as to discharge the excreta in the disposal space to the outside, wherein the body comprises the gender-specific module, which is detachably provided and comprises the urine disposal unit.

The gender-specific module includes at least one of a male module and a female module.

The male module includes a sexual organ insertion unit which has the urine disposal unit formed therein and is configured to surround a circumference of a sexual organ of male.

The urine disposal unit is partitioned by the excrement disposal unit.

The male module includes a connection unit configured to connect the sexual organ insertion unit to the body.

The female module includes a seat unit which has an urine disposal unit communicating with the excrement disposal unit and is formed to correspond to a curved shape of the genital area of female.

The apparatus further includes a spraying portion which is exposed to the disposal space and sprays washing water.

The apparatus further includes a flow channel switching unit which is provided in the accommodation space and supplies the washing water introduced from the outside to the spraying portion.

The spraying portion includes an upper side nozzle exposed to the urine disposal unit.

The spraying portion includes a rotary nozzle exposed to the excrement disposal unit.

Advantageous Effects

In order to solve the above-described problems, the present invention provides an excreta disposal apparatus comprising a gender-specific module having the following effects.

First, since the seating unit is formed to correspond to the curved shape of the genital area and buttocks of a user and can be adhered to the user's body, there is an advantage that the leakage of the excreta can be prevented in a state where the user wears the excreta disposal apparatus.

Secondly, since the main body unit also has a size corresponding to the width between the legs of the user, there is an advantage that the posture of the user can be maintained naturally.

Third, there is an advantage that the user's feelings of wearing is greatly improved.

Fourth, there is an advantage that the user is not restricted in the behavior even when the user wears the excreta disposal apparatus, and the posture can be freely changed.

Fifth, since a gender-specific module having a structure specialized for each gender is provided, there is an advantage that the structure can be changed to correspond to a body shape according to the gender of the patient.

The effects of the present invention are not limited to the effects mentioned above, and other effects not mentioned can be clearly understood by those skilled in the art from the description of the claims.

MODE FOR INVENTION

Figure 1:
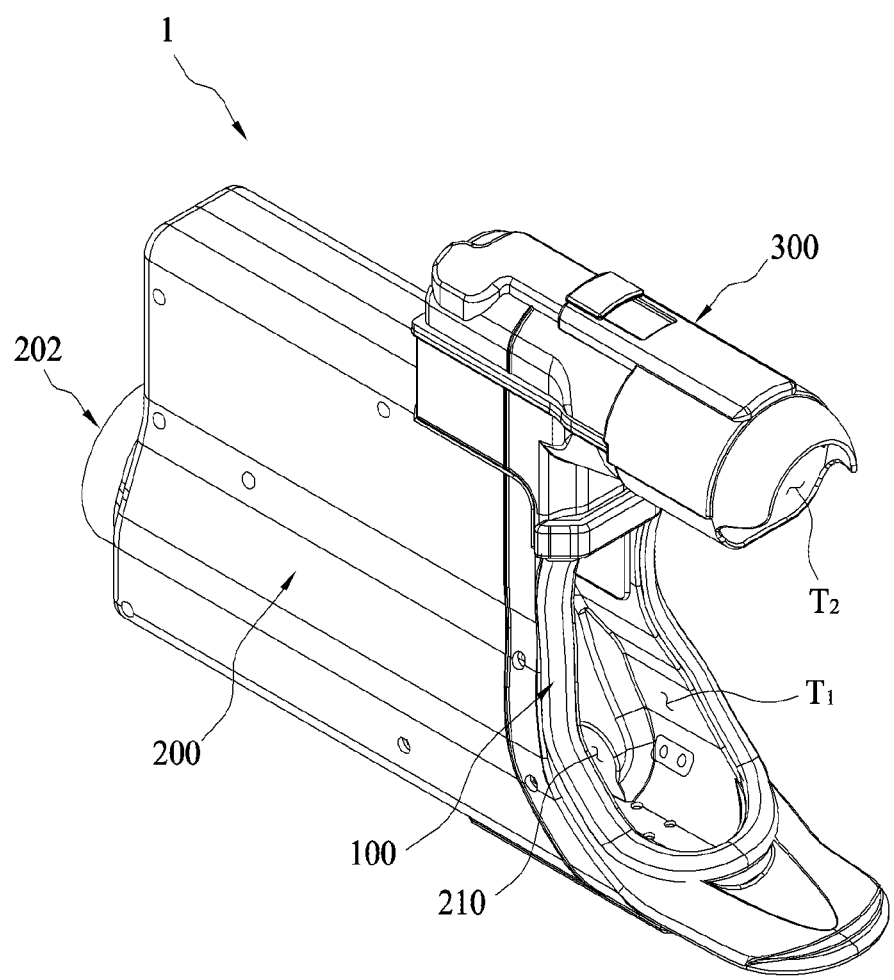
FIG. 1 is a perspective view showing an entire structure of an excreta disposal apparatus according to an embodiment of the present invention.

Hereinafter, preferred embodiments of the present invention will be described with reference to the accompanying drawings. In describing the present embodiment, the same designations and the same reference numerals are used for the same components, and further description thereof will be omitted.

FIG. 1 is a perspective view showing an entire structure of an excreta disposal apparatus 1 according to an embodiment of the present invention.

As shown in FIG. 1, the excreta disposal apparatus 1 according to an embodiment of the present invention includes a body including a seating portion 100 and a main body unit 200, and a discharge channel 210. The body may include a gender-specific module detachably mounted. The gender-specific module includes at least one of a male module and a female module. In the present embodiment, a male module is mounted.

The seating portion 100 has a curved shape corresponding to a curvature of the genital area and buttocks of a human body, and has disposal spaces T1 and T2 which are opened in the direction of the genital area and buttocks and receive the excreta discharged from the human body.

Here, the genital area of the human body refers to an area around the sexual organ of the male and female, and the buttocks are connected to the above-mentioned genital area and refers to an area around the anus. That is, the seating portion 100 is formed to be seated in the groin of the human body, and has a curved shape corresponding to the curvature.

The disposal spaces T1 and T2 are formed to have a certain volume so as to receive excreta including urine and excrement. The disposal spaces T1 and T2 of the present embodiment include a urine disposal unit T2 corresponding to the genital area of the human body and an excrement disposal unit T1 corresponding to the buttocks of the human body.

That is, in the case of the present embodiment, the disposal spaces T1 and T2 are partitioned by a male module 300 so as to separately dispose of urine and excrement. However, it is obvious that, when using the excreta disposal apparatus 1 by a woman, unlike the present embodiment, a female module may be used instead of the male module 300. In the case of the female module, the urine disposal unit and the excrement disposal unit may be connected without being partitioned. This will be described later.

The main body unit 200 is connected to the seating portion 100 so as to be mounted between the legs of the human body when a user wears the excreta disposal apparatus 1. That is, the user can stretch his/her legs to both sides of the main body unit 200 in a state in which the seating portion 100 is in close contact with the genital area and buttocks, so that the user can wear the excreta disposal apparatus 1 stably.

In addition, although not shown in the drawing, an accommodation space is provided inside the main body unit 200, and various elements may be provided in the accommodation space. This will be described later.

Meanwhile, for convenience of explanation, the open direction side of the disposal spaces T1 and T2 is defined as a front side, and the opposite direction is defined as a rear side. Further, the direction in which the urine disposal unit T2 is provided is defined as an upper side and the opposite direction is defined as a lower side.

The discharge channel 210 is provided in the accommodation space and communicates with the disposal spaces T1 and T2 to discharge the excreta of the disposal spaces T1 and T2 to the outside. Particularly, in the present embodiment, a through hole 202 is formed in the rear side of the main body unit 200 so that an external connection pipe can be inserted into the accommodation space.

The connection pipe may include an excreta flow pipe connected to suck excreta by using a separate suction device, a washing water feeding pipe for supplying washing water, and the like. That is, the discharge channel 210 is connected to the excreta flow pipe so that the excreta can be discharged to the outside.

Figure 2:
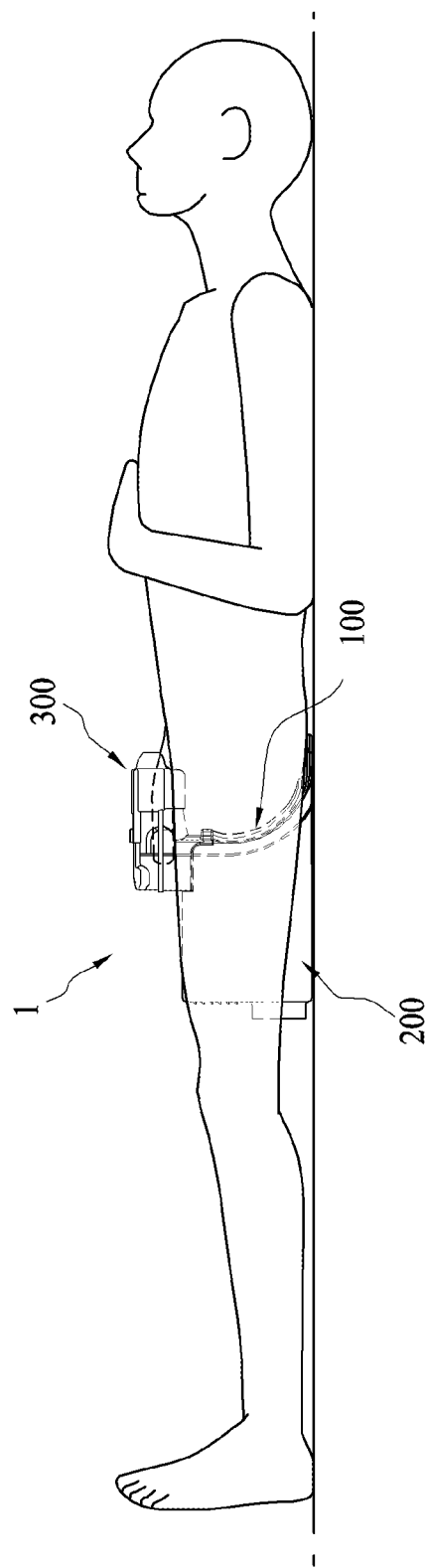
FIG. 2 is a side view of an excreta disposal apparatus worn on a human body according to an embodiment of the present invention.

FIG. 2 is a side view of an excreta disposal apparatus 1 worn on a human body according to an embodiment of the present invention.

As shown in FIG. 2, the user adheres the seating portion 100 to the genital area and buttocks while lying on a bed or the like, and stretches legs on both sides of the main body unit 200 to stably wear the excreta disposal apparatus. As described above, since the excreta disposal apparatus 1 according to an embodiment of the present invention is formed to correspond to the shape of the human body, there is no need for the user to change the posture forcibly according to the excreta disposal apparatus 1, and a natural posture can be maintained.

In addition, even if the user changes his/her posture from side to side or the like, it can be moved along the user's body without being detached, and does not interfere with user's movement in a state of being positioned between the user's legs even when the user moves.

Figure 3:
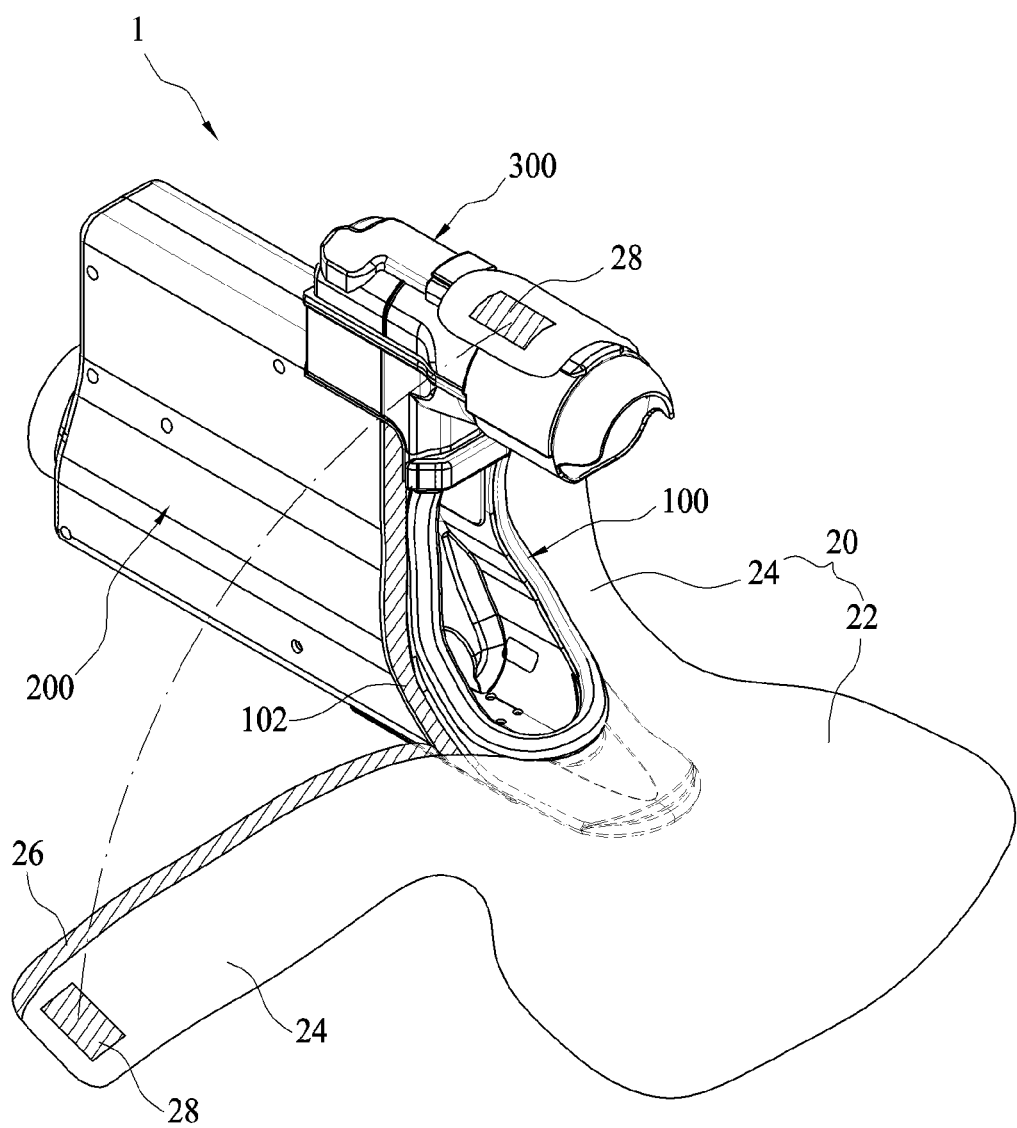
FIG. 3 is a perspective view showing a state where a pad is attached to a seating unit of an excreta disposal apparatus according to an embodiment of the present invention.

FIG. 3 is a perspective view showing a state where a pad 20 is attached to the seating portion 100 of the excreta disposal apparatus 1 according to an embodiment of the present invention.

As shown in FIG. 3, the excreta disposal apparatus 1 according to an embodiment of the present invention may include a pad 20 detachably installed to surround the seating portion 100. The pad 20 may be made of fabric or the like to improve the wearer's feeling of wearing, and may stably fix the excreta disposal apparatus 1 to the user's body.

In the case of the present embodiment, the pad 20 includes a pack portion 22 and a wing portion 24. The pack portion 22 is attached to the lower side of the seating portion 100 so as to surround the circumference of the user's buttocks. The wing portion 24 is attached so as to surround the circumference of the seating portion 100. Meanwhile, in order to attach the pad 20 to the seating portion 100, the seating portion 100 and the pad 20 may be provided with a velcro. That is, a seating unit velcro 102 and a pad velcro 26 are formed to correspond to each other, so that the pad 20 can be easily attached. In addition, in the present embodiment, each wing portion 24 is provided with a fixation velcro 28 so that respective wing portions 24 can be fixed to each other.

Figure 4:
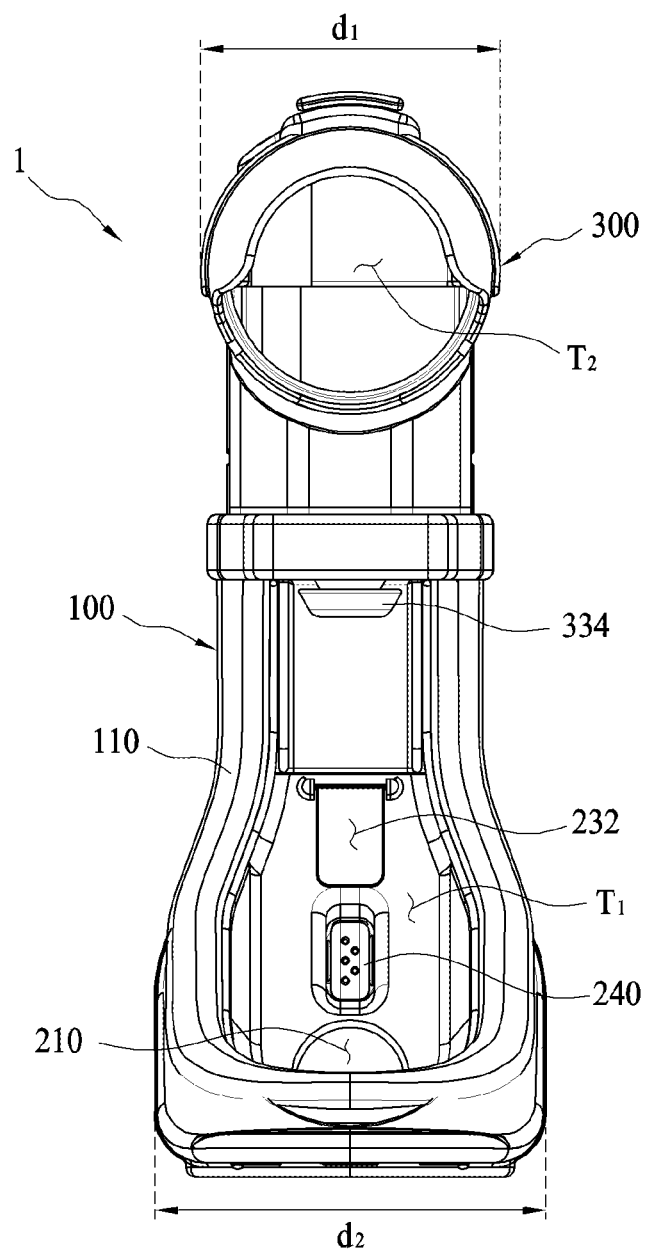
FIG. 4 is a front view of an excreta disposal apparatus according to an embodiment of the present invention.

FIG. 4 is a front view of the excreta disposal apparatus 1 according to an embodiment of the present invention.

FIG. 4 shows the disposal spaces T1 and T2 of the seating portion 100 in more detail. As described above, in the present embodiment, the disposal spaces T1 and T2 include the urine disposal unit T2 and the excrement disposal unit T1. Various elements for disposing of the excreta may be provided in the disposal spaces T1 and T2.

A spraying portion is an element that is exposed to the disposal spaces T1 and T2 to spray washing water, and may include one or more spraying nozzles. In the case of the present embodiment, the spraying portion is provided with a rotary nozzle 240 for spraying washing water to the excrement disposal unit T1 side, an auxiliary nozzle 334, and, although not shown, an upper side nozzle for spraying washing water to the urine disposal unit T2 side.

That is, the angle of the rotary nozzle 240 can be controlled to wash the periphery of the buttocks of the human body, and the auxiliary nozzle 334 sprays washing water so as to wash the surface of the excrement disposal unit T1. In addition, the upper side nozzle also sprays washing water to wash the genital area and the surface of the urine disposal unit T2.

In addition, in the present embodiment, a drying air jet opening 232 is formed in the disposal space T1 and T2 to allow a drying air to flow and be jetted, thereby rapidly drying the water after washing.

Meanwhile, as shown in the drawing, the body including the seating portion 100 and the main body unit is formed in such a manner that a width d1 of the upper portion is narrower than a width d2 of the lower portion when viewed from the front. That is, it has a shape corresponding to the curved shape of a thigh portion of the human body, so that both legs of the user can be stably adhered to both sides of the body of the excreta disposal apparatus 1. In addition, the body is formed to have a width corresponding to the width between the legs of the user, so that the user can take a natural posture without opening his/her legs forcibly.

In the present embodiment, a fastening member 110 is provided around the seating portion 100 to be in close contact with the user's body. The fastening member 110 is provided in a band shape along the circumferential line of the seating portion 100, so that the feelings of wearing can be improved.

Figure 5:
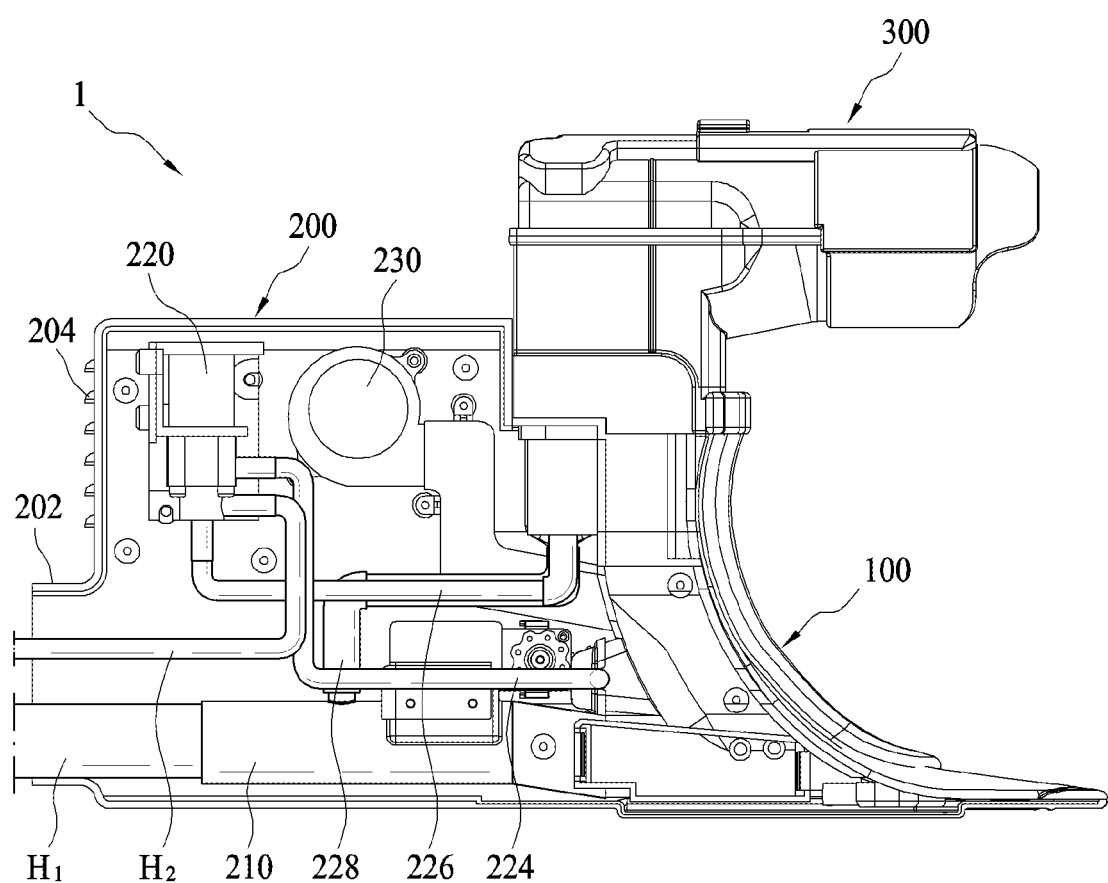
FIG. 5 is a cross-sectional view showing an internal structure of a main body unit in an excreta disposal apparatus according to an embodiment of the present invention.

FIG. 5 is a cross-sectional view showing an internal structure of the main body unit 200 in the excreta disposal apparatus 1 according to an embodiment of the present invention.

As shown in FIG. 5, an accommodation space is formed inside the main body unit 200, and the accommodation space may be provided with various elements. In the present embodiment, the accommodation space is provided with the above mentioned discharge channel 210, a flow channel switching unit 220, and an air blowing unit 230.

The discharge channel 210 is connected to an excreta flow tube H1 that is introduced through the through hole 202 to discharge the excreta to the outside. Particularly, in the present embodiment, the urine received from the male module 300 side can be introduced into the discharge channel 210 through an auxiliary discharge channel 228.

The flow channel switching unit 220 is an element which is connected to a washing water feeding pipe H2 introduced through the through hole 202 and receives the washing water from the outside, and ramifies and supplies the washing water to a plurality of spray nozzles through a solenoid valve or the like. Specifically, in the present embodiment, the washing water stored in the flow channel switching unit 220 may flow to the rotary nozzle through a first supply channel 224 and may flow to the auxiliary nozzle and the upper side nozzle through a second supply channel 226.

The air blowing unit 230 is an element which blows dry air to the disposal space, can generate dry air by using a blowing fan or the like, and can blow the dry air to the disposal space side through the drying air jet opening. Further, a heater may be further provided so as to increase the temperature of the dry air.

In the present embodiment, an air inlet 204 is formed on the rear surface of the main body unit 200 to allow an external air to flow to ventilate the inside of the accommodation space.

Hereinafter, the male module 300 provided in the present embodiment will be described in more detail.

Figure 6:
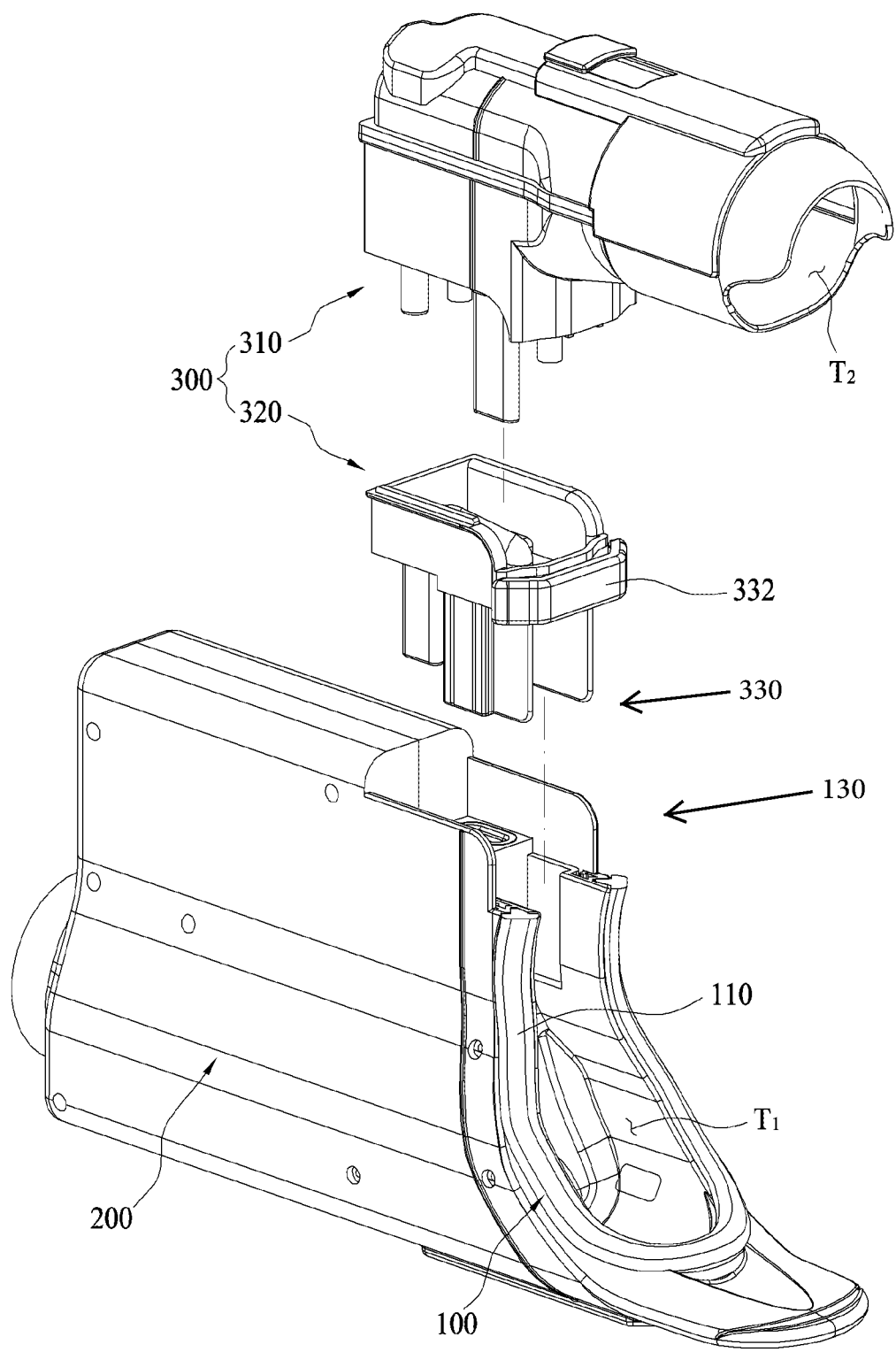
FIG. 6 is a perspective view showing a decomposition structure of a male module in an excreta disposal apparatus according to an embodiment of the present invention.

FIG. 6 is a perspective view showing a decomposition structure of the male module 300 in the excreta disposal apparatus according to an embodiment of the present invention.

As shown in FIG. 6, in the present embodiment, the male module 300 may include a sexual organ insertion unit 310 which has a urine disposal unit T2 formed therein and is configured to surround the circumference of a sexual organ of a male, and a rigid connector 330 for rigidly or stably connecting to a connection unit 320, which is configured to connect the sexual organ insertion unit 310 rigidly or stably to a receiving portion 130 of the seating portion or seating unit 100 of the body, as shown in FIG. 6 and as described below.

That is, the sexual organ insertion unit 310 has a shape corresponding to the shape of a sexual organ of the male, is rigidly or stably fixed to the body of the excreta disposal apparatus 1, and is formed to receive urine in a state where the sexual organ of the male is inserted. Accordingly, a sexual organ of the male having a high degree of freedom of movement can be stably fixed, so that the urine can be prevented from being indiscriminately discharged according to the direction of the sexual organ of the male and only a minimum range can be contaminated.

In the present embodiment, the urine disposal unit T2 is configured to be separated from the excrement disposal unit T1 by the male module 300, and the urine may be introduced into the discharge channel through the above mentioned auxiliary discharge channel. That is, it is possible to prevent the urine from entering the excrement disposal unit T1 and contaminating the user's buttocks.

As described above, in the present embodiment, the urine disposal unit T2 of the male module 300 is configured to be partitioned from the above mentioned excrement disposal unit T1, but the present invention is not limited thereto. That is, unlike the present embodiment, the urine disposal unit T2 may communicate with the excrement disposal unit T1, and in this case, the auxiliary discharge channel may not be separately provided.

Figure 7:
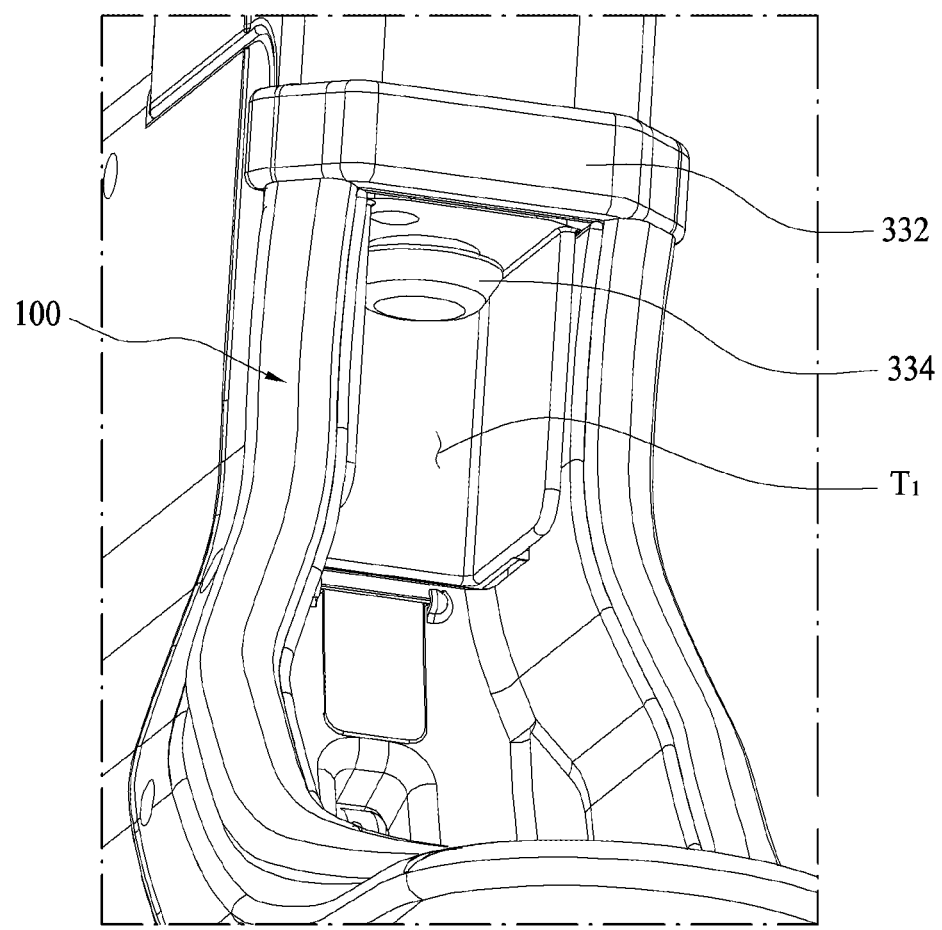
FIG. 7 is a perspective view of an auxiliary nozzle provided in a male module in an excreta disposal apparatus according to an embodiment of the present invention.

FIG. 7 is a perspective view of the auxiliary nozzle 334 provided in a male module in the excreta disposal apparatus according to an embodiment of the present invention.

As shown in FIG. 7, the male module may be provided with the auxiliary nozzle 334 which is exposed to the excrement disposal unit T1 side and sprays washing water. Since the auxiliary nozzle 334 is provided in the upper portion of the excrement disposal unit T1, it is possible to smoothly wash the entire surface of the excrement disposal unit T1.

At this time, the washing water supplied to the auxiliary nozzle 334 may flow into the male module from the above mentioned second supply channel and ramify to the auxiliary nozzle 334 side.

Meanwhile, an auxiliary contact member 332 connected to a body-side contact member may be provided on the lower portion of the male module. The auxiliary contact member 332 is provided to be in contact with the body-side contact member in a state where the male module is coupled to the body, so that the excrement disposal unit T1 can be sealed.

In the above, the male module was described. Hereinafter, another embodiment in which the female module is provided will be described.

Figure 8:
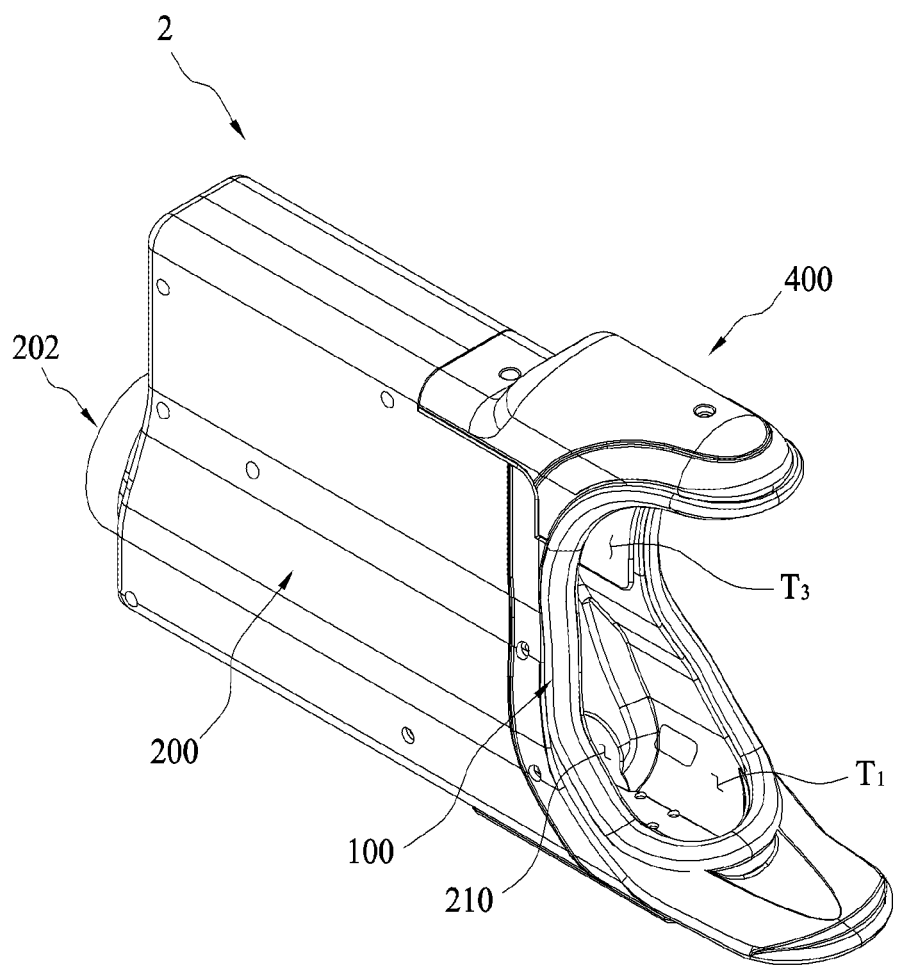
FIG. 8 is a perspective view showing an entire structure of an excreta disposal apparatus according to another embodiment of the present invention.

FIG. 8 is a perspective view showing an entire structure of an excreta disposal apparatus 2 according to another embodiment of the present invention.

As shown in FIG. 8, the body of the excreta disposal apparatus 2 according to another embodiment of the present invention includes a female module 400. Since the other elements excluding the female module 400 are the same as those of the above embodiment, only the female module 400 will be described below.

The female module 400 is provided with a urine disposal unit T3 communicating with the excrement disposal unit T1, and is formed to correspond to the curved shape of the genital area of the female. That is, in the case of a female, unlike male, since there is no movement of the sexual organ, the urine disposal unit T3 and the above-described excrement disposal unit T1 are formed as a single space to communicate with each other and able to simultaneously receive urine and excrement. Therefore, unlike the case of the male module, both the urine and the excrement can flow into the discharge channel 210 and be discharged.

Figure 9:
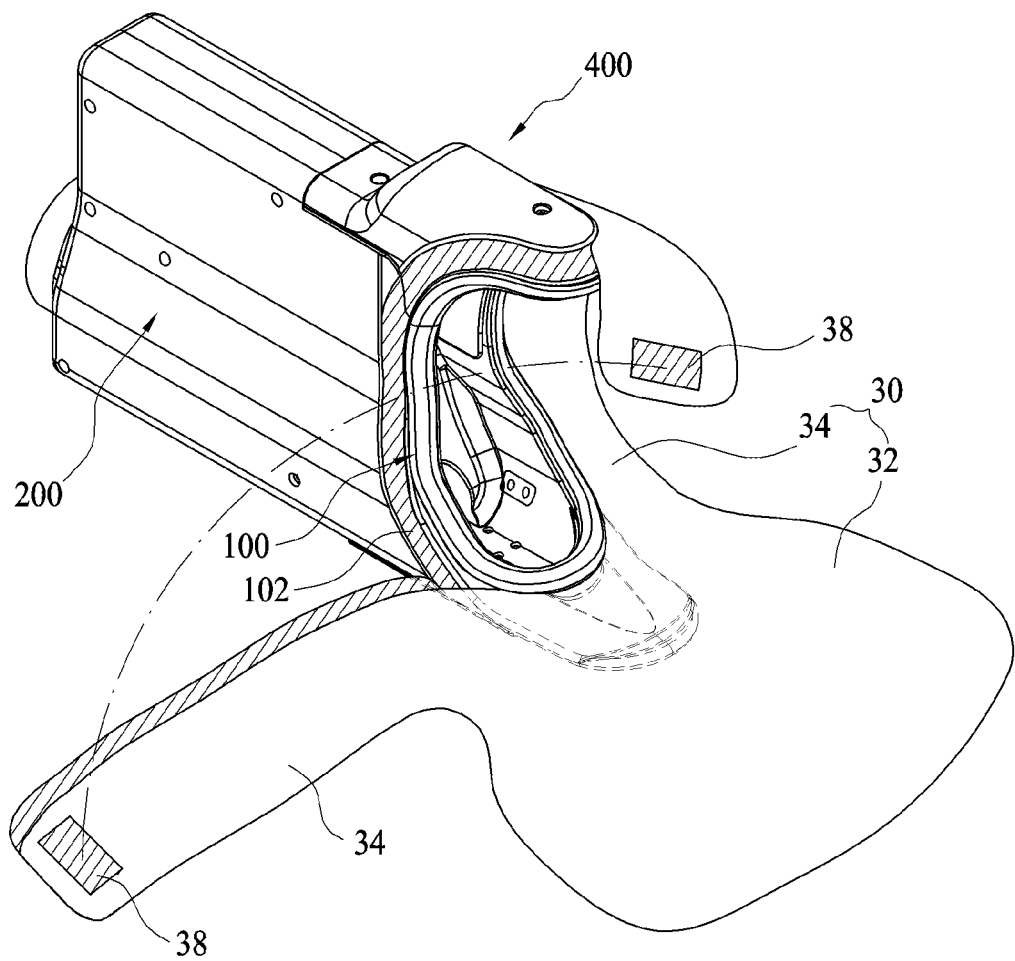
FIG. 9 is a perspective view showing a state where a pad is attached to a seating unit of an excreta disposal apparatus according to another embodiment of the present invention.

FIG. 9 is a perspective view showing a state where a pad 30 is attached to the seating portion 100 of the excreta disposal apparatus according to another embodiment of the present invention.

As shown in FIG. 9, in the present embodiment in which the female module 400 is combined, the seating unit velcro 102 is extended to the female module 400 side, and the pad side velcro is also configured to correspond to the length of the seating unit velcro 102 so as to surround the entire circumference of the seating portion 100. The pack portion 32, the wings 34, and the fixation velcro 38 are formed in the same manner as in the above-described embodiment.

Figure 10:
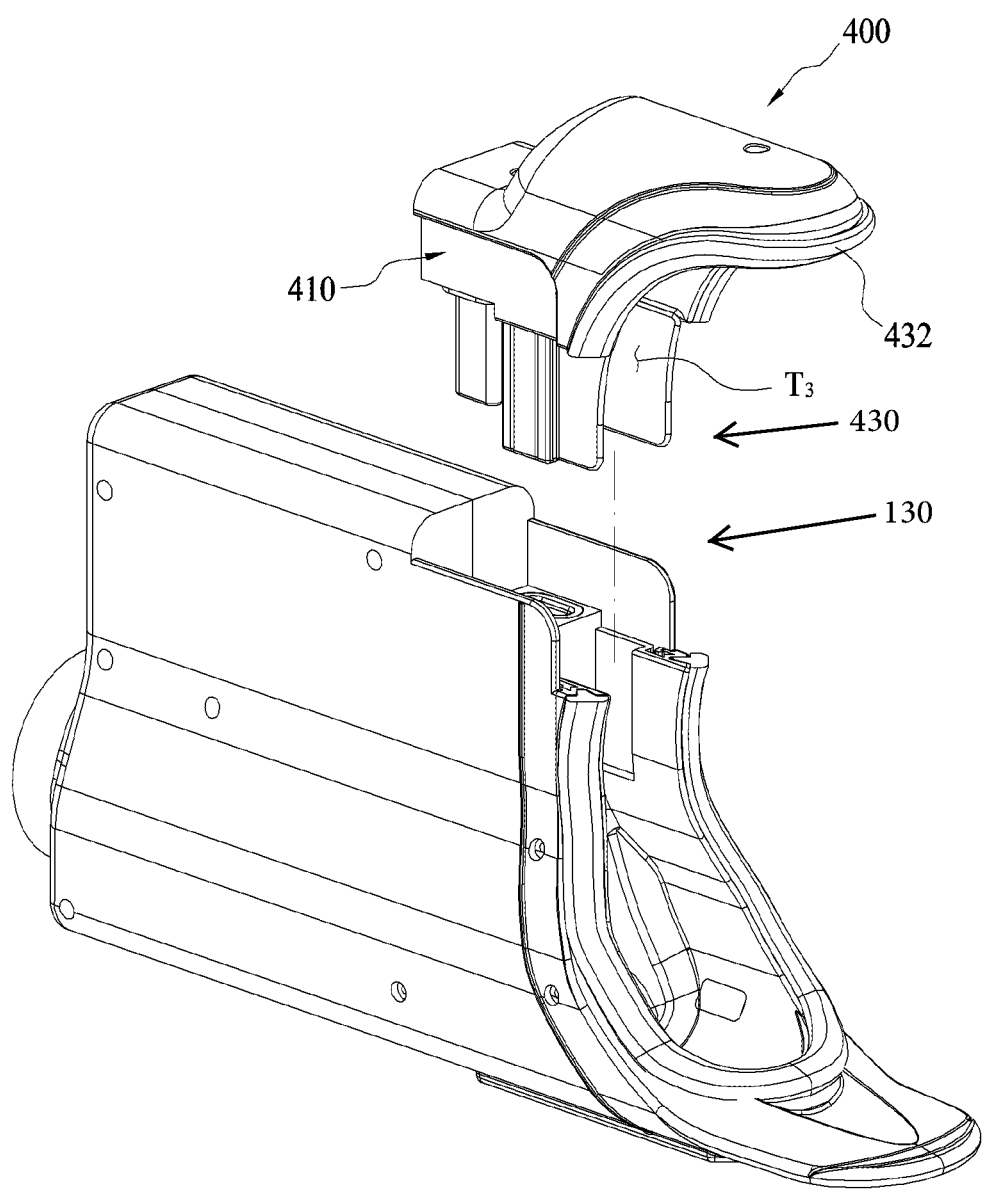
FIG. 10 is a perspective view showing a decomposition structure of a female module in an excreta disposal apparatus according to another embodiment of the present invention.

FIG. 10 is a perspective view showing a decomposition structure of a female module in the excreta disposal apparatus according to another embodiment of the present invention.

Figure 11:
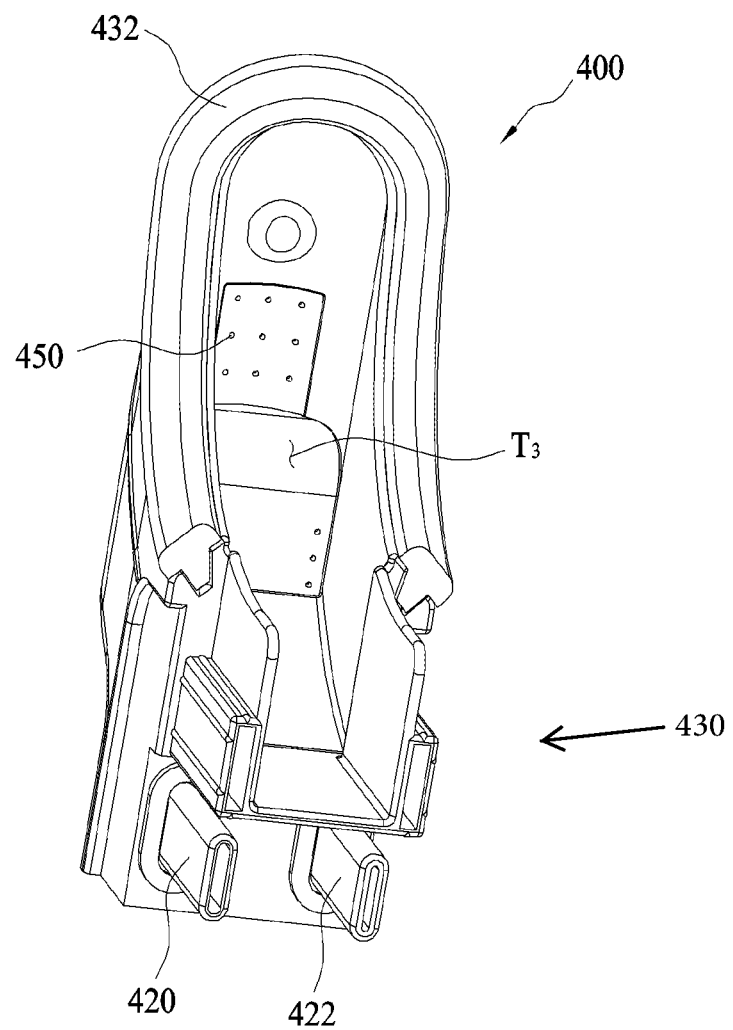
FIG. 11 is a perspective view showing an upper side nozzle provided in a female module in an excreta disposal apparatus according to another embodiment of the present invention.

As shown in FIGS. 10 AND 11, in the present embodiment, the female module 400 includes a seat unit 410 which has a rigid connector 430 for rigidly coupling the female seat unit 410 to the body by way of the receiving portion 130, has the urine disposal unit T3 formed therein, and is formed to correspond to the curved shape of the genital area of the female. As described above, the urine disposal unit T3 has an opened lower portion so as to communicate with the excrement disposal unit, forming a single opening with the excrement disposal unit, as shown in FIG. 10.

In the present embodiment, an auxiliary contact member 432, which is connected to the contact member of the body, is provided at a portion where the seat unit 410 is in contact with the human body. The auxiliary contact member 432 of the female module 400 is formed to extend the contact member of the body unlike the auxiliary contact member provided in the male module, and the female module 400 is formed in a closed curve shape together with the contact member in the state where the female module 400 is coupled to the body.

FIG. 11 is a perspective view showing an upper side nozzle 450 provided in the female module 400 in the excreta disposal apparatus according to another embodiment of the present invention.

As shown in FIG. 11, the female module 400 may include an upper side nozzle 450. The upper side nozzle 450 is provided on the inner side of the female module 400 so that the user can wash the genital area and the disposal space by spraying the washing water from the upper side while the user wears the excreta disposal apparatus.

The female module 400 may be provided with a delivery channel 420 for receiving the washing water from the above mentioned second supply channel so as to supply the washing water to the upper side nozzle 450. At this time, in the present embodiment, an auxiliary coupling 422 which can stably couple the female module 400 to the body in a form of being symmetrical with the delivery channel 420 may be further formed.

As described above, the present invention provides a gender-specific module having a specific structure according to each gender, so that it is possible to change the structure so as to correspond to the shape of human body according to the gender of the patient.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims. Accordingly, the scope of the present invention is not construed as being limited to the described embodiments but is defined by the appended claims as well as equivalents thereto.

The invention claimed is:

1. An excreta disposal apparatus comprising: a body comprising a seating unit, which has a shape corresponding to a curved shape of a genital area and buttocks of a human body having an anus, comprises a receiving portion rigidly attached to the seating unit for connecting gender specific modules corresponding to the genital area of the human body, and an excrement disposal unit corresponding to the buttocks of the human body which has a disposal space open toward the genital area and buttocks and the anus of the human body so as to take urine and feces discharged from the human body, and a main body unit, which is connected to the seating unit so as to be mounted between legs of the human body and has an accommodation space therein; and
 a discharge channel, which is provided in the accommodation space and communicates with the disposal space so as to discharge the urine and feces in the disposal space to the outside of the excreta disposal apparatus;
 wherein the gender specific modules include:
  a male module comprising a penis insertion unit which has a urine disposal unit formed therein, the penis insertion unit being formed to surround a circumference of a penis, and a rigid connector for rigidly coupling the male module to the receiving portion, and
  a female module comprising a female seat unit which has a urine disposal unit formed therein, and an auxiliary contact member disposed thereon, the female seat unit is formed to correspond to the curved shape of a female genital area, and has a rigid connector for rigidly coupling the female module to the receiving portion;
 wherein the receiving portion is detachably connectable to only one of the male module and the female module receiving portion at a given time, wherein:
 when the male module is connected to the receiving portion both the urine disposal unit and the excrement disposal unit are in fluid communication with the disposal space, and
 when the female module is connected to the receiving portion, the auxiliary contact member mates with a fastening member of the body of the excrement disposal apparatus to seal the excrement disposal unit and the urine disposal unit to the human body.

2. The apparatus of claim 1, further comprising a connection unit detachably engaging the male module and configured to connect the male module rigidly to the receiving portion, the connection unit having an auxiliary contact member disposed thereon for mating with the fastening member of the body of the excrement disposal apparatus to seal the excrement disposal unit of the excrement disposal apparatus to the human body.

3. The apparatus of claim 1, further comprising a spraying portion which is exposed to the disposal space and sprays washing water.

4. The apparatus of claim 3, further comprising a flow channel switching unit which is provided in the accommodation space and supplies the washing water introduced from the outside of the excrement disposal apparatus to the spraying portion.

5. The apparatus of claim 3, wherein the spraying portion comprises an upper side nozzle configured to be exposed to the urine disposal unit of the gender-specific module when the gender-specific module is connected to the receiving portion.

6. The apparatus of claim 3, wherein the spraying portion comprises a rotary nozzle exposed to the excrement disposal unit.

7. The apparatus of claim 1, wherein the urine disposal unit of the female seat unit has an opened lower portion forming a single opening with the excrement disposal unit when the female module is connected to the receiving portion.

* * * * *